(12) United States Patent
Pepys (10) Patent No.: US 7,390,795 B2
(45) Date of Patent: Jun. 24, 2008

(54) TREATMENT AND PREVENTION OF TISSUE DAMAGE

(75) Inventor: Mark B. Pepys, London (GB)

(73) Assignee: Pentraxin Therapeutics Limited, London (GB)

( * ) Notice: Subject to any disclaimer, the term of this patent is extended or adjusted under 35 U.S.C. 154(b) by 0 days.

(21) Appl. No.: 09/737,544

(22) Filed: Dec. 18, 2000

(65) Prior Publication Data

US 2003/0171251 A1 Sep. 11, 2003

(51) Int. Cl.
*A61K 31/685* (2006.01)
(52) U.S. Cl. .......................................... 514/77
(58) Field of Classification Search .............. 514/76–78
See application file for complete search history.

(56) References Cited

U.S. PATENT DOCUMENTS

| | | | | |
|---|---|---|---|---|
| 4,640,913 A | * | 2/1987 | Wissner et al. ................. | 514/77 |
| 5,064,817 A | * | 11/1991 | Yedgar et al. .................. | 514/78 |
| 5,681,829 A | | 10/1997 | Tempesta et al. | |
| 5,811,568 A | | 9/1998 | Bierer et al. | |
| 6,764,826 B2 | * | 7/2004 | Yeh et al. ...................... | 435/7.1 |

FOREIGN PATENT DOCUMENTS

| | | |
|---|---|---|
| WO | WO 01/94951 | 12/2001 |
| WO | WO 03/013508 | 2/2003 |

OTHER PUBLICATIONS

Kitao "Role of human C-reactive protein in lipid metabolism. Ingestion of CRP-lipoprotein complex by Macrophage," Rinsho Kagaku, 1992, 21 (4) 231-234, CAPLUS abstract, AN 1993:144839.*
Pepys, M.B. and Baltz, M.L. (1983) Acute phase proteins with special reference to C-reactive protein and related protein (pentaxins) and serum amyloid A protein. *Adv. Immunol.*, 34: 141-212.
Pepys, M.B. (1996) The acute phase response and C-reactive protein. In: *Oxford Textbook of Medicine, Third Ed.*, vol. 2 (Weatherall, D.J., Ledingham, J.G.G. and Warrell, D.A., eds.), Oxford University Press, Oxford, pp. 1527-1533.
Volanakis, J.E. and Kaplan, M.H. (1971) Specificity of C-reactive protein for choline phosphate residues of pneumococcal C-polysaccharide. *Proc. Soc. Exp. Biol. Med*, 136: 612-614.
de Beer, F.C., Soutar, A.K., Baltz, M.L., Trayner, I., Feinstein, A. and Pepys, M.B. (1982) Low density and very low density lipoproteins are selectively bound by aggregated C-reactive protein. *J. Exp. Med*, 156: 230-242.
Pepys, M.B., Rowe, I.F. and Baltz, M.L. (1985) C-reactive protein: binding to lipids and lipoproteins, *Int. Rev. Exp. Pathol.*, 27: 83-111.

(Continued)

*Primary Examiner*—Shengjun Wang
(74) *Attorney, Agent, or Firm*—Frommer Lawrence & Haug LLP; Thomas J. Kowalski; Angela M. Collison (57) ABSTRACT

A method for the treatment or prevention of tissue damage in a subject having an inflammatory and/or tissue damaging condition, which comprises administering to the subject an effective amount of a compound capable of inhibiting the binding of C-reactive protein (CRP) to an autologous or extrinsic ligand.

9 Claims, 2 Drawing Sheets

OTHER PUBLICATIONS

Narkates, A.J. and Volanakis, J.E. (1982) C-reactive protein binding specificities: artificial and natural phospholipid bilayers. *Ann. N. Y. Acad. Sci.*, 389: 172-182.

Volanakis, J.E. and Wirtz, K.W.A. (1979) Interaction of C-reactive protein with artificial phosphatidylcholine bilayers. *Nature*, 281: 155-157.

Du Clos, T.W. (1989) C-reactive protein reacts with the U1 small nuclear ribonucleoprotein. *J. Immunol.*, 143: 2553-2559.

Pepys, M.B., Booth, S.E., Tennent, G.A., Butler, P.J.G. and Williams, D.G. (1994) Binding of pentraxins to different nuclear structures: C-reactive protein binds to small nuclear ribonucleoprotein particles, serum amyloid P component binds to chromatin and nucleoli. *Clin. Exp. Immunol.*, 97: 152-157.

Kindmark, C.-O. (1972) In vitro binding of human C-reactive protein by some pathogenic bacteria and zymosan. *Clin. Exp. Immunol.*, 11: 283-289.

Fletcher, T.C., White, A. and Baldo, B.A. (1980) Isolation of a phosphorylcholine- containing component from the turbot tapeworm, *Bothriocephalus scorpii* (Muller) and its reaction with C-reactive protein. *Parasite Immunol.*, 2: 237-248.

de Beaufort, A.J., Langermans, J.A.M., Matze-van der Lans, A.M., Hiemstra, P.S., Vossen, J.M. and Van Furth, R. (1997) Difference in binding of killed and live *Streptococcus pneumoniae* serotypes by C-reactive protein. *Scand. J. Immunol.*, 46: 597-600.

Weiser, J.N., Pan, N., McGowan, K.L., Musher, D., Martin, A. and Richards, J. (1998) Phosphorylcholine on the lipopolysaccharide of *Haemophilus influenzae* contributes to persistence in the respiratory tract and sensitivity to serum killing mediated by C-reactive protein. *J. Exp. Med*, 187: 631-640.

Culley, F.J., Bodman-Smith, K.B., Ferguson, M.A.J., Nikolaev, AN., Shantilal, N. and Raynes, J.G. (2000) C-reactive protein binds to phosphorylated carbohydrates. *Glycobiology*, 10: 59-65.

Kaplan, M.H. and Volanakis, J.E. (1974) Interaction of C-reactive protein complexes with the complement system. I. Consumption of human complement associated with the reaction of C-reactive protein with pneumococcal C-polysaccharide and with the choline phosphatides, lecithin and sphingomyelin. *J. ImmunoL*, 112: 2135-2147.

Volanakis, J.E. and Kaplan, M.H. (1974) Interaction of C-reactive protein complexes with the complement system. II. Consumption of guinea-pig complement by CRP complexes: requirement for human Clq. *J. Immunol.*, 113: 9-17.

Claus, D.R., Siegel, J., Petras, K., Osmand, A.P. and Gewurz, H. (1977) Interactions of C-reactive protein with the first component of human complement. *J. Immunol.*, 119: 187-192.

Volanakis, J.E. (1982) Complement activation by C-reactive protein complexes. *Ann. N. Y. Acad Sci.*, 389: 235-250.

Mortensen, R.F., Osmand, A.P., Lint, T.F. and Gewurz, H. (1976) Interaction of C-reactive protein with lymphocytes and monocytes: complement-dependent adherence and phagocytosis. *J. Immunol.*, 117: 774-781.

Nakayama, S., Mold, C., Gewurz, H. and Du Clos, T.W. (1982) Opsonic properties of C-reactive protein in vivo. *J. Immunol.*, 128: 2435-2438.

Osmand, A.P., Mortensen, R.F., Siegel, J. and Gewurz, H. (1975) Interactions of C-reactive protein with the complement system. III. Complement-dependent passive hemolysis initiated by CRP. *J. Exp. Med*, 142: 1065-1077.

Finland, M. and Dowling, H.F. (1935) Cutaneous reactions and antibody response to intracutaneous injections of pneumococcus polysaccharides. *J. ImmunoL*, 29: 285-299.

Kushner, 1. and Kaplan, M.H. (1961) Studies of acute phase protein. I. An immunohistochemical method for the localization of Cx-reactive protein in rabbits. Association with necrosis in local inflammatory lesions. *J. Exp. Med*, 114: 961-973.

Kushner, I., Rakita, L. and Kaplan, M.H. (1963) Studies of acute phase protein. II. Localization of Cx-reactive protein in heart in induced myocardial infarction in rabbits. *J. Clin. Invest.*, 42: 286-292.

Gitlin, J.D., Gitlin, J.1. and Gitlin, D. (1977) Localisation of C-reactive protein in synovium of patients with rheumatoid arthritis. *Arthritis Rheum.*, 20: 1491-1499.

Du Clos, T.W., Mold, C., Paterson, P.Y., Alroy, J. and Gewurz, H. (1981) Localization of C-reactive protein in inflammatory lesions of experimental allergic encephalomyelitis. *Clin. Exp. Immunol.*, 43: 565-573.

Lagrand, W.K. Niessen, H.W.M., Wolbink, G-J., Jaspars, L.H., Visser, C.A., Verheugt, F.W.A., Meijer, C.J.L.M. and Hack, C.E. (1997) C-reactive protein colocalizes with complement in human hearts during acute myocardial infarction. *Circulation*, 95: 97-103.

Torzewski, J., Torzewski, M., Bowyer, D.E., Frohlich, M., Koenig, W., Waltenberger, J., Fitzsimmons, C. and Hombach, V. (1998) C-reactive protein frequently colocalizes with the terminal complement complex in the intima of early atherosclerotic lesions of human coronary arteries. *Arterioscler. Thromb. Vasc.* Biol., 18: 1386-1392.

Wolbink, G.-J., Bossink, A.W.J., Groeneveld, A.B.J., de Groot, M.C. M., Thijs, L.G. and Hack, C.E. (1998) Complement activation in patients with sepsis is in part mediated by C-reactive protein. *J. Infect. Dis.*, 177: 81-87.

Vigushin, D.M., Pepys, M.B. and Hawkins, P.N. (1993) Metabolic and scintigraphic studies of radioiodinated human C-reactive protein in health and disease. *J. Clin. Invest.*, 91: 1351-1357.

Kew, R.R., Hyers, T.M. and Webster, R.O. (1990) Human C-reactive protein inhibits neutrophil chemotaxis in vitro: possible implications for the adult respiratory distress syndrome. *J. Lab. Clin. Med*, 115: 339-349.

Heuertz, R.M., Xia, D., Samols, D. and Webster, R.O. (1992) Transgenic mice expressing plasma rabbit C-reactive protein exhibit diminished vascular permeability and neutrophil; infiltration in C5a-induced alveolitis. *FASEB J.*, 6: 1064 (abstract).

Mold, C. and Gewurz, H. (1980) Activation of the alternative pathway by liposomes: inhibitory effect of C-reactive protein. *Fed. Proc.*, 39: 702.

Mold, C. and Gewurz, H. (1981) Inhibitory effect of C-reactive protein on alternative C pathway activation by liposomes and *Streptococcus pneumoniae*. *J. Immunol.*, 127: 2089-2092.

Gershov, D., Kim, S., Brot, N. and Elkon, K.B. (2000) C-reactive protein binds to apoptotic cells, protects the cells from assembly of the terminal complement components, and sustains an antiinflammatory innate immune response: implications for systemic autoimmunity. *J. Exp. Med*, 192: 1353-1363.

Shine, B., de Beer, F.C. and Pepys, M.B. (1981) Solid phase radioimmunoassays for C-reactive protein. *Clin. Chim. Acta*, 117: 13-23.

Hutchinson, W.L., Koenig, W., Frohlich, M., Sund, M., Lowe, G.D. O. and Pepys, M.B. (2000) Immunoradiometric assay of circulating C-reactive protein: age-related values in the adult general population. *Clin. Chem.*, 46: 934-938.

Liuzzo, G., Biasucci, L.M., Gallimore, J.R., Grillo, R.L., Rebuzzi, A.G., Pepys, M.B. and Maseri, A. (1994) The prognostic value of C-reactive protein and serum amyloid A protein in severe unstable angina. *N. Engl. J. Med.*, 331: 417-424.

Kuller, L.H., Tracy, R.P., Shaten, J. and Meilahn, E.N. (1996) Relation of C-reactive protein and coronary heart-disease in the MRFIT nested case control study. *Am. J. Epidemiol.*, 144: 537-547.

Haverkate, F., Thompson, S.G., Pyke, S.D.M., Gallimore, J.R. and Pepys, M.B. (1997) Production of C-reactive protein and risk of coronary events in stable and unstable angina. *Lancet*, 349: 462-466.

Ridker, P.M., Cushman, M., Stampfer, M.J., Tracy, R.P. and Hennekens, C.H. (1997) Inflammation, aspirin, and the risk of cardiovascular disease in apparently healthy men. *N. Engl. J. Med*, 336: 973-979.

Ridker, P.M., Cushman, M., Stampfer, M.J., Tracy, R.P. and Hennekens, C.H. (1998) Plasma concentration of C-reactive protein and risk of developing peripheral vascular disease. *Circulation*, 97: 425-428.

Ridker, P.M., Buring, J.E., Shih, J., Matias, M. and Hennekens, C.H. (1998) Prospective study of C-reactive protein and the risk of future cardiovascular events among apparently healthy women. *Circulation*, 98: 731-733.

Ridker, P.M. (1998) C-reactive protein and risks of future myocardial infarction and thombotic stroke. *Eur. Heart J*, 19: 1-3.

Danesh, J., Collins, R., Appleby, P. and Peto, R. (1998) Association of fibrinogen, C-reactive protein, albumin, or leukocyte count with coronary heart disease. *J. Am. Coll. Cardiol.*, 279: 1477-1482.

Koenig, W., Sund, M., Frohlich, M., Fischer, H.-G., Lowel, H., Doring, A., Hutchinson, W.L. and Pepys, M.B. (1999) C-reactive protein, a sensitive marker of inflammation, predicts future risk of coronary heart disease in initially healthy middle-aged men. Results from the MONICA (Monitoring Trends and Determinants in Cardiovascular Disease) Augsburg Cohort Study 1984 to 1992. *Circulation*, 99: 237-242.

Danesh, J., Whincup, P., Walker, M., Lennon, L., Thomson, A., Appleby, P., Gallimore, J.R. and Pepys, M.B. (2000) Low-grade inflammation and coronary heart disease: new prospective studies and updated meta-analyses. *B.MJ*, 321: 199-204.

Zhang, YX, Cliff, W.J., Schoefl, G.I. and Higgins, G. (1999) Coronary C-reactive protein distribution: its relation to development of atherosclerosis. *Atherosclerosis*, 145: 375-379.

Bhakdi, S., Torzewski, M., Klouche, M. and Hemmes, M. (1999) Complement and atherogenesis. Binding of CRP to degraded, nonoxidized LDL enhances complement activation. *Arterioscler. Thromb. Vasc. Biol.*, 19: 2348-2354.

Cermak, J., Key, N.S., Bach, R.R., Balla, J., Jacob, H.S. and Vercellotti, G.M. (1993) C-reactive protein induces human peripheral blood monocytes to synthesize tissue factor. *Blood*, 82: 513-520.

de Beer, F.C., Hind, C.R.K., Fox, K.M., Allan, R., Maseri, A. and Pepys, M.B. (1982) Measurement of serum C-reactive protein concentration in myocardial ischaemia and infarction. *Br. Heart J*, 47: 239-243.

Ueda, S., Ikeda, U., Yamamoto, K., Takahashi, M., Nishinaga, M., Nago, N. and Shimada, K. (1996) C-reactive protein as a predictor of cardiac rupture after acute myocardial infarction. *Am. Heart J*, 131: 857-860.

Pietila, K.O., Harmoinen, A.P., Jokinftty, J. and Pasternack, A.I. (1996) Serum C-reactive protein concentration in acute myocardial infarction and its relationship to mortality during 24 months to follow-up in patients under thrombolytic treatment. *Eur. Heart J.*, 17: 1345-1349.

Morrow, D.A., Rifai, N., Antman, E.M., Weiner, D.L., McCabe, C.H., Cannon, C.P. and Braunwald, E. (1998) C-reactive protein is a potent predictor of mortality independently of and in combination with troponin T in acute coronary syndromes: a TIMI 11 A substudy. Thrombolysis in myocardial infarction. *J. Am. Coll. Cardiol.*, 31: 1460-1465.

Tommasi, S., Carluccio, E., Bentivoglio, M., Buccolieri, M., Mariotti, M., Politano, M. and Corea, L. (1999) C-reactive protein as a marker for cardiac ischemic events in the year after a first, uncomplicated myocardial infarction. *Am. J. Cardiol.*, 83: 1595-1599.

de Winter, R.J., Bholasingh, R., Lijmer, J.G., Koster, R.W., Gorgels, J.P.M.C., Schouten, Y., Hoek, F.J. and Sanders, G.T. (1999) Independent prognostic value of C-reactive protein and troponin I in patients with unstable angina or non-Q-wave myocardial infarction. *Cardiovasc. Res.*, 42: 240-245.

Nikfardjam, M., Miillner, M., Schreiber, W., Oschatz, E., Exner, M., Domanovits, H., Laggner, AN and Huber, K. (2000) The association between C-reactive protein on admission and mortality in patients with acute myocardial infarction. *J. Intern. Med.*, 247: 341-345.

Beranek, J.T. (1997) C-reactive protein and complement in myocardial infarction and postinfarction heart failure. *Eur. Heart J.*, 18: 1834-1835.

Beranek, J.T. (1998) C-reactive protein in postinfarction heart rupture. *Am. Heart J.*, 136: 563-564.

van Leeuwen, M.A., van Rijswijk, M.H., Sluiter, W.J., van Riel, P.L.C.M., Kuper, I.H., van de Putte, L.B.A., Pepys, M.B. and Limburg, P.C. (1997) Individual relationship between progression of radiological damage and the acute phase response in early rheumatoid arthritis. Towards development of a decision support system. *J. Rheumatol.*, 24: 20-27.

Boralessa, H., de Beer, F.C., Manchie, A., Whitwam, J.G. and Pepys, M.B. (1986) C-reactive protein in patients undergoing cardiac surgery. *Anaesthesia*, 41: 11-15.

Shrive, A.K., Cheetham, G.M.T., Holden, D., Myles, D.A.A., Turnell, W.G., Volanakis, J.E., Pepys, M.B., Bloomer, A.C. and Greenhough, T.J. (1996) Three-dimensional structure of human C-reactive protein. *Nature Struct. Biology*, 3: 346-354.

Thompson, D., Pepys, M.B. and Wood, S.P. (1999) The physiological structure of human C-reactive protein and its complex with phosphocholine. *Structure*, 7: 169-177.

Griselli, M., Herbert, J., Hutchinson, W.L., Taylor, K.M., Sohail, M., Krausz, T. and Pepys, M.B. (1999) C-reactive protein and complement are important mediators of tissue damage in acute myocardial infarction. *J. Exp. Med.*, 190: 1733-1739.

Bhakdi, S., Dorweiler, B., Kirchmann, R., Torzewski, J., Weise, E., Tranum-Jensen, J., Walev, I. and Wieland, E. (1995) On the pathogenesis of atherosclerosis: enzymatic transformation of human low density lipoprotein to an atherogenic moiety. *J. Exp. Med*, 182: 1959-1971.

Hawkins, P.N., Tennent, G.A., Woo, P. and Pepys, M.B. (1991) Studies in vivo and in vitro of serum amyloid P component in normals and in a patient with AA amyloidosis. *Clin. Exp. Immunol.*, 84: 308-316.

Hawkins, P.N., Wootton, R. and Pepys, M.B. (1990) Metabolic studies of radioiodinated serum amyloid P component in normal subjects and patients with systemic amyloidosis. *J. Clin. Invest.*, 86: 1862-1869.

de Beer, F.C., Baltz, M.L., Munn, E.A., Feinstein, A., Taylor, J., Bruton, C., Clamp, J.R. and Pepys, M.B. (1982) Isolation and characterisation of C-reactive protein and serum amyloid P component in the rat. *Immunology*, 45: 55-70.

Pepys, M.B., Tompkins, C. and Smith, A.D. (1979) An improved method for the isolation from *Naja naja* venom of cobra factor (CoF) free of phospholipase A. *J. Immunol. Methods*, 30: 105-117.

Nelson, S.R., Tennent, G.A., Sethi, D., Gower, P.E., Ballardie, F.W., Amatayakul-Chantler, S. and Pepys, M.B. (1991) Serum amyloid P component in chronic renal failure and dialysis. *Clin. Chim. Acta*, 200: 191-200.

Pepys, M.B. (1975) Studies in vivo of cobra factor and murine C3. *Immunology*, 28: 369-377.

Pepys, M.B., Dash, A.C., Fletcher, T.C., Richardson, N., Munn, E.A. and Feinstein, A. (1978) Analogues in other mammals and in fish of human plasma proteins C-reactive protein and amyloid P component. *Nature*, 273: 168-170.

Baltz, M.L., de Beer, F.C., Feinstein, A., Munn, E.A., Milstein, C.P., Fletcher, T.C., March, J.F., Taylor, J., Bruton, C., Clamp, J.R., Davies, AJ.S. and Pepys, M.B. (1982) Phylogenetic aspects of C-reactive protein and related proteins: *Ann. N. Y. Acad Sci.*, 389: 49-75.

Mold, C., Nakayama, S., Holzer, T.J., Gewurz, H. and Du Clos, T.W. (1981) C-reactive protein is protective against *Streptococcus pneumoniae* infection in mice. *J. Exp. Med.*, 154: 1703-1708.

Yother, J., Volanakis, J.E. and Briles, D.E. (1982) Human C-reactive protein is protective against fatal *Streptococcus pneumoniae* infection in mice. *J. Immunol.*, 128: 2374-2376.

Bickerstaff, M.C.M., Botto, M., Hutchinson, W.L., Herbert, J., Tennent, G.A., Bybee, A., Mitchell, D.A., Cook, H.T., Butler, P.J.G., Walport, M.J. and Pepys, M.B. (1999) Serum amyloid P component controls chromatin degradation and prevents antinuclear autoimmunity. *Nature Med.*, 5: 694-697.

Steel et al., "The major acute phase reactants: C-reactive protein, serum amyloid P component and serum amyloid A protein", immunology Today (1994) 15:81-89.

Kilpatrick et al., "Molecular Genetics, Structure and Function of C-reactive Protein," Immunol. Res. (1991) 10:43-53.

Bhakdi et al., "Possible Protective role for C-Reactive Protein in Atherogenesis," Circulation, p. 1870-1876, (2004a).

Bhakdi et al., "Beyond cholesterol: the cnigma of atherosclerosis revisited," Thromb, Haemost., p. 639-645, (2004b).

Vadas et al., "Inhibition of human group II phospholipase A2 by C-reactive protein in vitro." J. Lipid Mediat. Cell Signal, vol. 11 (No. 2), p. 187-200 (abstract only), (1995).

Tsujimoto et al., "C-Reactive protein induced agglurination of lipid suspensions prepared in the presence and absence of phosphatidylcholine," J. Biochem., vol. 87 (No. 5), p. 1531-7 (abstract only), (1980).

Moriet al., "Involvements of fibronectin and lysophosphatidylcholine for selective binding of c-reactive protein," Cell Mol Biol., vol. 37 (No. 4), p. 421-31 (abstract only), (1991).

Chang et al., "C-reactive protein binds to both oxidized LDL and apoptotic cells through recognition of a common ligand:

Phosphorylcholine of oxidized phospholipids," Proc. Natl. Acad. Sci. U.S.A., vol. 99 (No. 20), p. 13043-8, (2002).

Gill et al., "Human C-Reactive Protein Increases Cerebral Infarct Size After Middle Cerebral Artery Occlusion in Adult Rats," J. Cerebral Blood Flow & Metabolism, vol. 24 (No. 11), p. 1214-1218, (Nov. 2004).

Berman et al., "Binding of C-reactive protein to nucleated cells leads to complement activation without cytolysis," J. Immunol., 1986, 136(4):1354-9.

Mold et al., "Regulation of complement activation by C-reactive protein," Immunopharmacology, 1999, 42:23-30.

Wang et al., "Synthesis and Properties of a Bipolar, Bisphosphatidyl Ethanolamine That Forms Stable 2-Dimensional Self-Assembled Bilayer Systems and Liposomes," J. Org. Chem., American Chemical Society, p. 4140-4147, (May 4, 1999).

Lu et al., "Synthetic Analogues of Irlbacholine: A Novel Antifungal Plant Metabolite isolated from *Irlbachia alata*," J. Nat. Prod., American Chemical Society and American Society of Pharmacognosy, p. 824-828, (May 19, 1999).

* cited by examiner

TREATMENT AND PREVENTION OF TISSUE DAMAGE

The present invention relates to a method for the treatment or prevention of tissue damage in a subject, especially a human subject having an inflammatory and/or tissue damaging condition. Compounds are provided for the treatment or prevention of the tissue damage, as well as methods for selecting and producing such compounds.

C-reactive protein (CRP) is a normal plasma protein of the pentraxin protein family, the other member of which is the very closely similar molecule, serum amyloid P component (SAP)[1]. CRP is the classical acute phase protein, the circulating concentration of which increases dramatically in response to most forms of inflammation, tissue injury and infection, and the value attained in most conditions correlates closely with the extent and activity of disease[2]. CRP is a calcium dependent ligand binding protein, the ligand which it binds wish highest affinity being phosphocholine residues[3], but it also binds a variety of other ligands. It binds many of its ligands with high avidity. Known ligands for CRP include both autologous and extrinsic structures. Autologous ligands include native[4,5] and modified plasma lipoproteins, damaged cell membranes[6], a number of different phospholipids and related compounds[7], and small nuclear ribonucleoprotein particles[8,9]. Extrinsic ligands include many glycan, phospholipid and other components of micro-organisms, such as capsular and somatic components of bacteria, fungi and parasites, as well as plant products[10-15]. When CRP has bound to its ligands it becomes capable of activating complement by the classical pathway via Clq[16-19] and achieving activation and fixation of C3, the main adhesion molecule of the complement system[20,21], as well as engagement of the terminal lytic phase, C5-C9[22].

Whilst very early clinical work[23] suggested that CRP might possibly contribute to inflammation, and subsequent experimental animal studies were interpreted as showing a pro-inflammatory role for CRP, there has hitherto been no direct evidence of any involvement of CRP in processes of inflammation and tissue damage. There are a few reports of CRP deposition in inflammatory and necrotic tissue lesions, and of association between CRP and complement activation[24-30]. However none of these studies shows directly that CRP is responsible for tissue damage, and the only study of real time CRP deposition in human tissues in living patients showed that it occurred only in trace amounts, if at all[31]. Indeed the published work that directly examines the role of CRP in experimental models of disease indicates that CRP may have an anti-inflammatory role that down-regulates infiltration of inflammatory cells and reduces tissue damage[32,33]. This would be consistent with she finding that complexed CRP is relatively inefficient at generating the terminal phase of complement activation and that involvement of CRP down-regulates other potentially inflammatory aspects of complement activation[34,35]. Very recent work in different models involving handling of apoptotic cells also indicates that CRP has anti-inflammatory properties[36]. There is thus certainly no consensus about the role of CRP in vivo and the predominant view is that it may be anti-inflammatory. In general the association of increased CRP production with disease conditions has hitherto been interpreted on the basis that CRP production reflects the severity of the underlying disease and/or the presence of intercurrent complications.

Atherosclerosis is extremely prevalent in developed countries and its major complications of myocardial infarction and stroke together account for about one third of all deaths. Although there have been advances in understanding of some aspects of pathogenesis and in prophylactic and post-event salvage treatments, the personal, social and economic burden of these conditions remains enormous. Similarly, chronic inflammatory diseases of unknown aetiology are common, debilitating, expensive and often dangerous to treat symptomatically, as well as being incurable and often shortening life expectancy. For example, rheumatoid arthritis affects about 4% of the population over the age or 50 years and, as well as being painful and causing severe disability, it is associated with significant premature mortality. The cancer burden is very heavy, accounting for about one third of all deaths in developed countries, and the severity and importance of infectious disease throughout the world is evident. There is a pressing need for new drugs to reduce severity and to prolong survival in all these different conditions.

Accordingly, in a first aspect, the present invention provides a method for the treatment or prevention of tissue damage in a subject having an inflammatory and/or tissue damaging condition, which comprises administering to the subject an effective amount of a compound capable of inhibiting the binding of C-reactive protein (CRP) to an autologous or extrinsic ligand.

As reported herein, it has been found for the first time that CRP does play a direct pathogenetic role in a disease condition, specifically by enhancing the extent of myocardial damage produced by ischemic injury. This pathogenetic role can be treated or prevented by the use of a drug capable of inhibiting the binding of CRP to its target ligand in vivo. Without wishing to be bound by theory and as described in further detail herein, it is thought that the inhibition of binding of CRP to its target ligand in vivo would prevent CRP from activating complement and thereby reduce or eliminate the deleterious effects of CRP mediated complement activation now thought responsible for tissue damage in the conditions to we treated according to the present invention.

In one embodiment according to the invention, the inflammatory and/or tissue damaging condition comprises atherosclerosis.

Whilst CRP is produced in large amounts in response to most forms of tissue injury, inflammation and infection, its circulating concentration is extremely low in normal healthy subjects and in most individuals in the general population[37,38]. Until recently these low levels were not considered to be of any clinical significance and he generally available assays for CRP were designed only to detect and measure circulating CRP when the concentration exceeded 5 or even 10 mg/l, representing the 90-99$^{th}$ centile of the range found in healthy subjects. However a large body of work has accumulated since our original discoveries, starting in 1994[39], that shows convincingly that even within the reference range for CRP, among values previously considered to be "normal", increased production of CRP is very significantly associated with atherothrombotic events, including myocardial infarction, stroke and progression of vascular disease[40-48].

The mechanisms underlying the association between even modestly increased CRP production and development, progression and complications of atherosclerosis, are not known. However it is likely to be highly relevant that atherosclerosis is known to be an inflammatory condition, and that CRP and activated complement are co-deposited in virtually all atheromatous plaques[29,49]. Furthermore, CRP selectively binds to low density lipoprotein (LDL), the major lipoprotein that accumulates in the arterial lesions of atherosclerosis[4,5], and binding of CRP to "modified", that is partly degraded, LDL such as is found in the plaques, potently activates complement[50]. Finally there is evidence that CRP can stimulate macrophages, which are the most abundant cells infiltrating atheromatous plaques, to produce tissue factor (TF)[51]. TF is the initiator of blood coagulation responsible for initiation of the thrombus formation on ruptured plaques that actually occludes atherosclerotic arteries and precipitates myocardial infarction or stroke. CRP may thus directly contribute to the pathogenesis, progression and clinically significant complications of atherosclerosis.

Once myocardial infarction has occurred, all patients mount a major acute phase response of CRP and the peak value attained is very significantly prognostic of outcome, that is complications and death, over the ensuing days, weeks and months[52-58]. Given the universal co-deposition of CRP and activated complement within the infarct itself, this strongly suggests that CRP contributes importantly to the extent and severity of the ischaemic pathology[28,59,60]. CRP values, and particularly cumulative production of CRP over time, are also very significantly predictive of progression, severity and complications of chronic inflammatory diseases of unknown aetiology, such as rheumatoid arthritis[61] and Crohn's disease, of acute and chronic bacterial, viral, fungal and parasitic infections, of ischaemic and necrotic diseases such as acute pancreatitis, and of many forms of cancer (reviewed in [1,2]). Even in the context of elective surgery, pre-operative CRP values and post-operative CRP production predict complications and outcome[62]. Our observations in atherosclerosis, and especially in the rat model of myocardial infarction exacerbated by human CRP, now indicate that CRP slay actually be actively contributing to disease severity in all these different conditions.

In a further embodiment, the inflammatory and/or tissue damaging condition is selected from an infection, an allergic complication of infection, an inflammatory disease, ischemic or other necrosis, traumatic tissue damage and malignant neoplasia.

For example, where the condition is an infection, this may be a non-protozoal infection such as a bacterial or viral infection. Where the condition is an allergic complication of infection, this may be selected from rheumatic fever, glomeorulonephritis and erythema nodosum leprosum. Where the condition is an inflammatory disease, this may be selected from rheumatoid arthritis, juvenile chronic (rheumatoid) arthritis, ankylosing spondylitis, psoriatic arthritis, systemic vasculitis, polymyalgia rheumatica, Reiter's disease, Crohn's disease and familial Mediterranean fever. Where the condition involves ischaemic or other necrosis selected from myocardial infarction, tumour embolization and acute pancreatitis. Where the condition is traumatic, this may be selected from acute or elective surgery, burns, chemical or physical injury, and fractures. Where the condition is malignant neoplasia, this may be selected from lymphoma, Hodgkin's disease, carcinoma and sarcoma.

According to the present invention, drugs that either inhibit the binding of CRP to its ligands in vivo, and/or that reduce its availability for such binding in vivo, will block the contribution of CRP to pathogenesis of disease and will thereby reduce extent and severity of disease, reducing symptoms and prolonging survival. The present invention provides for identification and testing of compounds with such effects, for the preparation of a composition for the prevention and/or treatment of atherosclerosis and its complications, including myocardial infarction, stroke and peripheral vascular disease, acute and chronic inflammatory diseases of known and unknown aetiology, acute and chronic infections of all types, traumatic injuries including burns, acute and elective surgery, malignant neoplasia of all types, and all disease conditions associated with increased CRP production.

Accordingly, in a further aspect, the present invention provides a method for selecting a pharmaceutical compound for treating or preventing tissue damage in a subject having an inflammatory and/or tissue damaging condition, which comprises contacting C-reactive protein (CRP) with a ligand thereof under conditions to permit CRP ligand binding, in the presence of a test compound; and selecting the test compound as the pharmaceutical compound if the test compound inhibits its binding of CRP to the ligand.

The present invention further provides a process for the production of a pharmaceutical agent. This process comprises (1) identifying a pharmaceutical compound by selecting the compound as described above; and (2) producing a pharmaceutical agent by providing a pharmaceutical compound or a pharmaceutical-acceptable derivative thereof.

The present invention is therefore concerned with a method for selecting a pharmaceutical compound which includes testing for CRP ligand binding in the presence of a test compound. Any test compound which inhibits binding of SAP to the ligand is selected as a potential pharmaceutical. For example, the test compound may be selected in the sense that it is identified and can then be produced on a larger scale by chemical or biochemical synthesis or may be physically selected for direct formulation as a pharmaceutical. In accordance with the process for production of the pharmaceutical agent, the test compound may be formulated for pharmaceutical use or may be derivatised or chemically modified to produce a pharmaceutically-acceptable derivative thereof. Such derivatisation may simply be required to incorporate new functional groups or alter existing functional groups to make the agent easier to formulate, for example by altering the solubility of the compound. Derivatisation of this nature may be used to decrease the toxicity of the compound, to alter the stability of the compound or even to modify the pharmacological activity thereof. Any such derivatised or modified compound may need to be retested according to the method of the present invention.

In the step of contacting CRP with the ligand, the conditions must be sufficient to permit CRP ligand binding in the absence of the test compound. In this way, where CRP ligand binding does not occur in the presence of the test compound, or occurs to a smaller extent than expected, this affect can be attributed to the test compound. It should be noted here that inhibition of binding should be broadly construed and is not limited to any particular mechanism; any reduction of the extent of binding constitutes inhibition of binding according to the present invention. Inhibition of binding is generally measured with reference to a control value (maximum binding in absence of test compound) and it is preferred that the $IC_{50}$ be low micromolar or less, more preferably nanomolar or less. Contacting takes place under conditions which include sufficient free calcium ions to permit the specific calcium dependent binding of CRP. A preferred buffer for the contacting is physiological buffered saline. CRP may be provided in pure or isolated form, or incorporated in whole serum.

The order in which the CRP, ligand and test compound are contacted together is not critical. All three components can be mixed at essentially the same time or two of the three components can be mixed and perhaps pre-incubated before addition of the third component. Contacting generally takes place under conditions in which at least one of the components is in the liquid phase. It is convenient, however, for either the CRP or the ligand to form part of a solid phase so that, in the testing procedure, phase separation car, be used as a technique to separate bound species from unbound species to facilitate testing for the extent of CRP ligand binding.

Accordingly, it is preferred that a first component comprising one of CRP or the ligand is present as part of a solid phase, which is contacted with a second component comprising the other as part of a liquid phase. The step of testing for CRP ligand binding may then comprise detecting binding of the second component to the solid phase. Detecting binding of the second component to the solid phase may be effected either by detecting the presence of the second component on the solid phase or by determining he amount of second component unbound to the solid phase and deducing from the amount of second component originally applied to the solid phase the amount actually binding to the solid phase.

According to this embodiment, the solid phase preferably comprises the first component attached to a solid support, which solid support may comprise a particulate support or a solid surface In a convenient embodiment, the solid surface comprises an interior surface of the container such as a microtitre plate well.

Conveniently, the step of testing for CRP ligand binding further comprises washing the solid phase to remove unbound material.

The second component may be labelled with a detectable label such as a radiolabel, a fluorochrome or an enzyme, as discussed herein. Alternatively, the binding of the second component to the solid phase may be detected immunologically either by antibody binding to the second component as bound to the solid phase or by quantitative immunological determination of the amount of second component not bound to the solid phase.

The present invention provides in vitro spot tests, low throughput, and high throughput screening procedures for detecting compounds with the capacity to inhibit binding of CRP, from man or other animals, to any and all of its known biological and chemical ligands. These methods are suitable for screening compound libraries of natural compounds of organic, inorganic and biological origin, as well as chemical libraries created by conventional synthesis or any form of combinatorial chemistry. They are also suitable for analysis of the mechanism of inhibition of CRP binding, and for evaluation of potency of inhibition during chemical and medicinal chemistry development of potential or actual pharmaceutical products from lead compounds identified by screening or spot testing. The present invention also comprises in vivo methods for testing effects and potency of CRP-inhibitory compounds on CRP binding, plasma turnover and catabolism in man and experimental animals, and on experimental models of disease that are exacerbated by human CRP.

Accordingly, in a further aspect, the present invention provides a method for selecting a pharmaceutical compound for treating or preventing tissue damage from a plurality of test compounds which comprises providing an array of reaction zones and a plurality of test compounds, and selecting the pharmaceutical compound by performing the above method of selecting the compound in each reaction zone.

Suitable compounds may be bound by CRP and thereby block the site of interaction between CRP and the target ligand, or they may bind to CRP to alter its structure thereby to inhibit or prevent binding to the ligand, or they may bind to the ligand and thereby mask it and prevent its recognition by CRP. The CRP molecule has a specific calcium-dependent binding site through which it binds to its ligands, and we have characterised this at atomic resolution by X-ray crystallography[63,64]. A major class of compounds that can be identified using the present invention comprises substances that are bound by the calcium-dependent ligand binding site of CRP so as to interfere with binding of CRP to its ligands. Our knowledge of the 3D structure of the binding site and the mechanism by which it binds its ligand provides for molecular design of model compounds for the purpose of the present invention, using for example the methods described in WO95/05394 and more recent refinements of structure-based drug design that have subsequently been developed. The same processes can be applied to improve the properties of lead compounds discovered during screening of libraries and other collections of candidate compounds. In particular, the hydrophobic cleft adjacent to the site In which phosphocholine, the highest affinity natural ligand for CRP, is bound, is a suitable target for drug design[64].

The present invention also provides for detection and study of compounds that inhibit CRP binding by the other mechanisms listed above. Furthermore, since the goal of treatment and/or prevention of disease using inhibitors of CRP binding is to prevent CRP from binding to its pathophysiologically relevant ligands in vivo, another class of compounds, which may or may not overlap with those described above, comprises substances that modify the availability of CRP in vivo, for example, by accelerating its clearance from the plasma so that the circulating concentration of CRP is greatly reduced.

One general class of compound suitable for use in the method of present invention has general Formula (I):

(I)

wherein X is H or an organic substituent group, and Y is N substituted to form ammonium.

X is typically H or a hydrocarbyl substituent optionally containing one or more of O, S or N. The hydrocarbyl substituent may be an alkyl group and is preferably unbranched. The hydrocarbyl substituent may have up to 20 carbon atoms and is advantageously lipophilic. For example, X is preferably H or $C_1$ to $C_{20}$, more preferably $C_{12}$ to $C_{20}$ alkyl. A particularly preferred embodiment is where X is a hexadecyl group.

It is preferred that Y is N—$R_3$ in which each R is independently selected from $C_1$ to $C_9$ alkyl. According to this embodiment R is advantageously methyl. Alternatively, two of the R groups may denote a $C_2$ to $C_5$ alkylene, optionally containing O, S or N.

Particularly preferred compounds include phosphocholine (where X=H and each R=$CH_3$) and hexadecyl phosphocholine (where X=$C_{16}$ alkyl and each R=$CH_3$)

The above class of chemical compounds, including methods of manufacture, are described in U.S. Pat. No. 5,990,915, which is directed to the use of these compounds in the treatment of leishmaniasis.

The invention will now be described in further detail, by way of example only, with reference to the following Examples and Experiments, and the accompanying drawings, in which.

EXAMPLES

Methods for Showing Binding of CRP to Autologous and Extrinsic Ligands.

In order to identify compounds that inhibit binding of CRP to ligands that may be relevant to the pathogenetic role or CRP, it is first necessary to have methods for showing such binding.

1] Binding of CRP to Autologous and Extrinsic Ligands.

For the purposes of this invention, the binding of CRP to various ligands can be demonstrated directly by allowing CRP, provided either by whole acute phase human or animal serum, or in isolated purified form, to contact ligands of human, animal, microbial or parasitic origin, or ligands derived by chemical synthesis. Examples of such ligands include native and modified forms of natural or synthetic lipids, phospholipids, glycolipids, glycans, proteoglycans, lipoproteins, proteins, peptides, nucleic acids, oligonucleotides, mononucleotides, plasma and other cellular membrane constituents, small nuclear ribonucleoprotein particles and other cell nuclear components, phosphocholine, phosphoethanolamine and related compounds, phosphate, sulphate, carboxylate and other polyanions. Contact must take place in physiological buffered saline containing sufficient free calcium ions (about 2 mmol/l). The potential ligands, can be in particulate form or immobilized on particles, such as agarose, acrylamide, polystyrene, latex, cellulose, or other beads, or on membranes, filters, or plastic or other solid surfaces such as microtitre plates or individual tubes. Immobilization may be by direct non-specific adherence of the ligand to the particles or surfaces, or by covalent attachment via amino, hydroxy, or other chemical groups on the ligand molecules being coupled directly or via spacer linkers to the solid phase material. After contacting the solid or immobilised ligands, CRP that has not bound is washed away with the same buffer in which binding took place, and the presence of CRP bound to the ligands is detected and quantified. Washing involves phase separation, such as centrifugation of solid particles, or immersion, flow through or flow over of solid surfaces such as membranes, filters, and plastic or other surfaces. Bound CRP ray be detected directly if the source of CRP contains CRP that has been labelled with a detectable marker. Such markers include gamma-emitting isotopes such as $^{125}$I or $^{131}$I for detection in a gamma counter; beta-emitting isotopes such as $^{14}$C or $^{3}$H for detection in a beta or scintillation counter; fluorochromes for detection in a fluorimeter, flow cytometer, or fluorescence activated cell sorter; enzymes such as peroxidase or alkaline phosphatase for detection by their specific catalytic actvity. In all of these cases it is essential to demonstrate that the process of directly labelling the CRP does not alter its physiological binding properties. This is done, for example, by comparing the binding of labelled and unlabelled CRP to an immobilised solid phase ligand, such as phosphoethanolamine or phosphocholine attached using a carbodiimide to carboxyhexyl-Sepharose™. Binding of CRP can also be demonstrated directly by immunochemical assay showing depletion of CRP from, the offered source of CRP, and recovery of the bound CRP when, after first washing with calcium containing buffer, the ligand material is eluted with buffer containing EDTA to chelate calcium ions. Alternatively, bound CRP may be detected indirectly, using antibodies raised in rabbits, sheep, goats, rats, mice, guinea pigs or other animals, specific for the CRP of the species being tested. For this purpose the anti-CRP antibodies may themselves be directly labelled with a radioactive isotope, enzyme, fluorochrome or other detectable marker, or the binding of anti-CRP antibodies to bound CRP may be detected using a second antibody directed against the immunoglobulin of the species of the primary anti-CRP reagent. In addition to detection and counting in instruments appropriate for the marker used, binding of CRP to microorganisms or their components may be visualised directly or indirectly using light, fluorescence or electron microscopy. Enzyme labelled CRP or anti-CRP antibodies can be used for light or electron microscopy, fluorochrome labelled reagents for fluorescence microscopy, and gold (or other electron dense particle) labelling for electron microscopy.

2] Binding of Autologous or Extrinsic Ligands by CRP.

An alternative approach to demonstration of ligand binding by CRP is to immobilize the CRP on a solid phase and then allow it to bind ligands that are either directly labelled or that can be detected, for example using specific antibodies directed against these ligands. Thus isolated purified CRP from man or other animals can be immobilized on beads, particles, membranes, filters, or plastic or other solid surfaces, by direct non-specific adherence or by covalent coupling, or by trapping with specific anti-CRP antibodies immobilized on the solid phase. Using the conditions specified in 1] above, potential ligands can then be contacted to the immobilized CRP and allowed to be bound by it.

Inhibition of CRP Binding to Microbial and Other Ligands

Any of the methods set out in 1] and 2] above for showing ligand binding by CRP can be used to test the capacity of compounds to inhibit such binding. However the speed and ease of use of the different techniques vary greatly, as well as their suitability for different purposes. Thus for screening large numbers of compounds, high throughput methods, such as those based on microtitre plates, are essential. A typical method of this type involves having ligand immobilized on the plates, and offering to each well an amount of radiolabelled CRP under conditions such that about 40% of it is bound. Compounds to be tested are added to the wells and preincubated in them before addition of the labelled CRP, and the effect of their presence on subsequent binding of CRP is monitored. In another configuration, the compounds to be tested are preincubated with the labelled CRP before the mixture is added to the plates. The reverse configuration, in which the CRP is immobilized, is also informative. Here the test compounds are preincubated with the immobilized CRP before the detectable ligand is added. These different approaches enable detection of compounds that block ligand binding by CRP by different mechanisms, and help to distinguish between those that are themselves specific ligands for CRP, those that affect the CRP molecule in other ways, and those that interact with the ligand to prevent its recognition by CRP. The calcium dependent ligand binding site of CRP is very well characterised and compounds bound by it that block binding of CRP to model ligands are virtually certain to also block binding of CRP to pathologically and therapeutically relevant ligands. However for the purpose of this invention, screening and subsequent development and testing involves parallel use of assays including pathophysiological and model ligands. Furthermore there may be compounds that differ in the range of interactions between CRP and pathophysiological ligands that they inhibit. Such compounds will be of greater therapeutic value in some diseases than others, and this can only be established by testing in in vivo animal models and eventually in clinical situations.

Direct Interaction Between CRP and Test Compounds

For the purposes of the present invention, another method to identify compounds that are bound by, or themselves bind to CRP, either in a calcium dependent fashion or independently of calcium, is the use of surface plasmon resonance (SPR). Purified CRP immobilized within an SPR instrument gives a quantifiable signal when it is exposed to another molecule that forms a complex with the CRP, and this is distinct from the absence of such a signal if no complex is formed. This technique allows compounds to be screened for their capacity to interact with CRP, and does not depend on any specific mode of interaction with CRP, in particular involving the calcium dependent ligand binding site of CRP, so it detects molecules that might not be found in test systems that require calcium dependent CRP binding.

Effects on CRP In vivo of Compounds that Block CRP-ligand Binding In vitro or Interact with CRP in Other Ways.

For the purpose of the present invention, compounds that block binding of CRP to its ligands, or that interact with CRP in other ways, are tested in vivo in mice and other experimental animals for their effects on plasma CRP concentrations and the turnover and catabolism of CRP. Having established by the administration of graded doses that the compounds are not intrinsically toxic, they are given in a range of doses to inbred mice of the C57EL/6, CBA, Balb/c, or other inbred or outbred strains. Serum is taken at regular intervals for immunochemical assay of CRP. Trace radiolabelled human CRP, or in separate experiments CRP from other species, is injected intravenously at different times in relation to the drug dosage, and both whole body counting and blood sampling is performed to monitor the plasma half life and whole body clearance of CRP. Plasma CRP concentration can also be monitored by specific immunoassay, in which case native unlabelled CRP tracer can be used. In addition the tracer CRP is preincubated with different amounts of the compounds being tested, and then injected into mice not receiving any drug, in order to test the effect drug binding has on CRP clearance. The effect of compounds on CRP in vivo is also tested in mice transgenic for human or rabbit CRP, and expressing the corresponding protein under the control of its own or another promoter or control sequence. Blood samples are taken at intervals before and after administration of different drug doses, whilst increased CRP production is induced either by an inflammatory stimulus or however the relevant promoter is triggered. According to the present invention, compounds that accelerate CRP clearance in vivo and/or lower plasma CRP concentration, thereby reducing in vivo availability of CRP, will be of therapeutic value.

Effects of CRP Blocking and/or Binding Compounds on Pathogenicity of CRP In vivo.

For the purpose of the present invention, compounds that block birding of CRP to its ligands, or that interact with CRP in other ways, are tested in vivo in mice and other experimental animals for their effects on models of disease in which human CRP exacerbates pathogenesis. For example, administration of human CRP to rats in which the coronary artery is ligated to induce myocardial infarction, markedly increases morbidity, mortality and the infarct size[65]. CRP interactive compounds for the purpose of the present invention, when given at the same time as the human CRP, abrogate this enhancement of pathology and protect against its clinical consequences. The same experimental test, with regard to myocardial infarction induced by coronary artery ligation, is conducted in wild type mice, to which human CRP is administered, and in human CRP transgenic mice. Compounds are also tested in corresponding rat and mouse models of acute and chronic infection, inflammation, trauma and other pathologies that are exacerbated by the presence of human CRP.

Atherosclerosis is induced in wild type C57BL/6 and other mouse strains by provision of a high fat diet, and takes place in an accelerated and enhanced form in mice with targeted deletion of the gene for the LDL receptor or for apolipoprotein E. In all these models, development and severity of atherosclerosis is enhanced by intercurrent systemic inflammation, and probably also by passive administration or transgenic production of human CRP. CRP interactive compounds for the purpose of the present invention are therefore tested in these models to show that they abrogate the enhanced atherosclerosis engendered by human CRP.

Compounds that block CRP binding to pathophysiologically relevant ligands in experimental animals in vivo and/or reduce availability of CRP in vivo, and that have then undergone formal toxicity testing and found to be acceptable for administration in man, are evaluated for their effects on plasma CRP concentration, half life, turnover and catabolism in human subjects Isolated human CRP is trace radiolabelled with $^{125}$I and injected intravenously, followed by plasma and urine turnover studies, as described elsewhere[31], and total plasma CRP concentration is also monitored immunochemically.

Inhibition of Binding and/or Availability of C-reactive Protein (CRP) In vivo as a Therapeutic Modality in Disease.

The present invention relates to methods for identification of chemical compounds that inhibit binding, and/or the availability for binding in vivo, of the plasma protein, C-reactive protein (CRP), to molecular ligands of autologous or extrinsic origin. Any such compounds or their derivatives that are acceptable for pharmaceutical use, being suitable for the treatment and prevention of atherosclerosis, atherothrombotic events, including myocardial infarction, stroke and peripheral vascular disease, and all types of inflammatory or tissue damaging diseases of known or unknown cause which are associated with increased production of CRP.

Screening for Inhibitors of Binding of $^{125}$I Radiolabelled CRP to Enzyme Modified Low Density Lipoprotein Immobilized in Microtitre Plates.

Introduction

The most specific known ligand of CRP, that is bound by it with highest affinity, is phosphocholine. However, likely critical ligands of importance in vivo in the pathogenesis of atherothrombosis, are modified forms of low density lipoprotein. The goal of therapy with a drug capable of inhibiting pathogenic effects of CRP in vivo is to prevent binding of CRP to such ligands. An assay to detect such compounds was therefore established and used to test hexadecyl phosphocholine, the candidate compound of the present invention.

Materials and Methods

Low density lipoprotein isolated from normal human serum by the standard ultracentrifugation method was subjected to partial enzymatic digestion with trypsin, cholesterol esterase, and neuraminidase according to the method of Bhakdi[50,66].

It was then dialysed into 0.05 M borate buffer, pH 8.0, and 10 μg total protein in 100 μl volumes were dispensed into the wells of Costar DNA-bind N-oxysuccinimide surface amine binding stripwell plates, and incubated at room temperature for 1 h. All wells were then washed three times with 200 μl volumes of PBS before blocking by incubation for 1 h at room temperature with 100 μl per well of 0.2 m Tris pH 8.0. The wells were then washed again 3 times with 200 μl volumes of PBS and finally emptied before adding to each one 100 μl volumes of the following reagents. For control uninhibited maximal binding: a standard dose of radiolabelled CRP[31] in 0.01M Tris buffered 0.14M NaCl/0.002M $CaCl_2$ at pH 8.0 containing 1% w/v BSA (TCB buffer). For background, non-specific, non-calcium dependent, binding in the presence of EDTA: the same dose of radiolabelled CRP in 0.01M Tris buffered 0.14M NaCl at pH 8.0 containing 10 mM EDTA, 1% w/v BSA (TEB buffer). For testing of inhibitors: the standard dose of radiolabelled CRP that had been pre-incubated in TCB at room temperature for 15 min with the various concentrations of test compounds shown in the Table. The plates were then sealed and incubated overnight at 37° C. in a sealed moist chamber, before 3 final washes with 200 μl per well volumes of TCB or TEB, followed by air drying for 1 h at room temperature, and then counting bound radiolabelled CRP.

The compounds tested in the experiment shown here were phosphocholine, which is known to be the best natural ligand for CRP, phosphoethanolamine, to which CRP is also well know to bind, and phosphoserine, a related phosphorylated molecule the binding to which of CRP has not previously been reported. These were compared with hexadecyl phosphocholine, the candidate inhibitor of CRP binding for use as a drug in vivo according to the present invention Results The capacity of the compounds tested to inhibit binding of CRP to enzyme modified low density lipoprotein is expressed as the percentage by which CRP binding was reduced compared to binding in the absence of any inhibitor (Table 1). All binding was inhibited by EDTA, confirming the specific, calcium dependent, nature of the interaction. Binding to control wells without the specific E-LDL ligand was at the same background level as seen with complete inhibition by EDTA. Phosphoethanolamine, a well known ligand of SAP produced inhibition at high concentration, but only modest effects when diluted. Phosphocholine, as expected, was the most potent inhibitor of CRP binding, but hexadecyl phosphocholine was also effective, with $IC_{50}$ value in the micromolar range and as active or more than phosphoeohanolamine. Hexadecyl phosphocholine is thus suitable for further testing as an drug to inhibit pathogenetic effects of CRP in vivo, according to the present invention.

Experiment

Mediation of Tissue Damage by CRP and Complement in Acute Myocardial Infarction.

This experiment demonstrates that parenteral injection of human CRP markedly enhances tissue damage, via a complement dependent mechanism, in experimental acute myocardial infarction produced by coronary artery ligation.

Materials and Methods

Protein Reagents and Assays. Human CRP[31], human serum amyloid P component (SAP)[68], rat CRP[69], rat C3[69] and cobra (Naja naja) venom factor[70] were isolated, purified and/or assayed precisely as previously described. The preparations of human CRP and SAP, and of cobra venom factor used in vivo were all >99% pure.

Induction and Measurement of Myocardial Infarction. Female Wistar rats bred at ICSM, Hammersmith campus were used at age 9-10 wk and weighed 230-280 g. Within each experiment the whole body and heart weights were the same in control and experimental groups. All animals were carefully examined and were healthy before being fasted overnight prior to surgery. General anesthesia was induced with inhaled isoflurane and supplemental oxygen was provided at 1.0 liter/min. The chest was opened through the sixth intercostal space, anesthesia was discontinued but supplemental oxygen continued at 0.5 liter/min, and the pericardium was opened to allow the heart to be lifted cut of the thorax. The left anterior descending coronary artery was immediately ligated at a constant distance just below the atrium with a 5/0 silk suture, the heart was replaced and the chest closed whilst active ventilation with 100% oxygen was continued. The duration of pneumothorax was about 30 s. Resuscitation was completed by gentle chest massage with the rat lying supine and there was usually rapid recovery of consciousness and of the righting reflex. Buprenorphine 0.05 mg/kg was given immediately for post-operative analgesia and repeated 12 hourly. Development of myocardial infarction was confirmed by early post-operative 4 lead electrocardiogram showing marked ST segment elevation in leads I and aVL as well as various arrhythmias.

Intra-operative and immediate post-operative mortality was up to 20%, but thereafter there were few deaths prior to day 5 when the rats were killed for measurement of infarct size. Deep anesthesia was induced with isoflurane and the hearts were excised while still beating in sinus rhythm and immediately arrested in diastole by immersion in 10 ml of 30 mM KCl. They were then cleaned of any extraneous adherent tissue and weighed before being briefly chilled at −20° C. to produce sufficient rigidity to facilitate cutting into defined sections. Each heart was cut into four slices of equal thickness perpendicular to the course of the left coronary artery, starting from the apex of the heart and ending at the position of the ligature around that artery. These slices were designated A, B, C, and D starting from the apex, and each was washed with pure water and then immersed in 0.02 M phosphate buffer pH 7.4 containing 0.5 mg/ml of nitroblue tetrazolium (NBT) (Sigma) at 37° C. for 30 min. NBT stains viable but not infarcted myocardium.

After staining with NBT the slices were washed briefly in cold water before fixation in 10% buffered formalin for 48 h, and the proximal cut surface of each slice was then imaged under standard conditions with a high resolution digital camera. The captured images were coded and analyzed 'blind' without knowledge by the operators of the treatment received by the rat in question. Lines were drawn around the total area of the slice, the NBT negative infarct zone, and any parts of the image to be excluded from the estimation including valves, chordae tendinae, shadows and edges, and the area of the infarct was determined as a percentage of the total area. The infarcts were confined to slices B, C and D, and the mean percentage in these three was taken as the infarct size in that heart. Statistical significance of differences between infarct sizes in different treatment groups within each experiment were sought by one way ANOVA and by Bonferroni t-tests.

In Vivo Treatments. Complement depletion was induced in vivo by a single i.p. injection of cobra venom factor at 250 U/kg. Human CRP or SAP were injected i.p. at 40 mg/kg 1 h after coronary artery ligation and then at 24 h intervals until the rats were killed on day 5. The proteins were dissolved in 10 mM Tris, 140 mM NaCl, pH 8.0, also containing 2 mM $CaCl_2$ in the case of human CRP, and the control rats received injections of the buffer alone at the same intervals. In one experiment rats were killed at 24, 48 and 72 h after coronary artery ligation or analysis of the effect of cobra venom factor on plasma C3, the usual dose was given and normal, unoperated cats were bled from the tail at intervals up to 6 d. For measurement of plasma clearance of human CRP and SAP, normal unoperated rats received a single 40 mg/kg dose of each protein and were bled at intervals up to 72 h later. Plasma clearance of human CRP was also studied in the same protocol in normal unoperated rats that had received cobra venom factor 24 h previously. These experiments could not be done in rats which had undergone coronary artery ligation because they do not survive the anesthesia required for bleeding, but there is no reason to suppose that the results in them would be significantly different.

Immunohistochemical Analysis. The formalin fixed heart slices were embedded in wax and sectioned at 2 μm thickness for routine hematoxylin and eosin staining and for immunohistochemical staining. Optimal dilutions of the IgG fractions of monospecific goat anti-human CRP, rabbit anti-rat CRP and sheep anti-rat C3 antisera, raised by immunization with the respective isolated pure antigens, were used as primary antibodies after blocking the sections by incubation in 20% vol/vol normal serum of the species of origin of the secondary antibody. In all cases endogenous peroxidase activity was blocked by incubation with $H_2O_2$ before testing. Secondary antibodies were optimal dilutions or goat anti-rabbit IgG or rabbit anti-goat IgG (both from Dako), which cross-reacts with sheep IgG. Finally rabbit or goat peroxidase-anti-peroxidase complexes (Dako) were used followed by visualization with diaminobenzidine. All positive staining was completely abolished when the primary antibodies had been absorbed before use with an excess of the respective specific antigen. In the case of rat C3, which was not available ire pure form, parallel absorptions of the sheep anti-rat C3 antibody were performed with normal rat serum and with C3 depleted serum from a cobra venom treated rat. The latter did not affect anti-C3 staining whilst C3 sufficient rat serum abolished it completely. In order to confirm that the antigens under investigation were not affected by formalin fixation and tissue processing, sample hearts were snap frozen without fixation and 5 μm cryostat sections were cut for immunoperoxidase staining. For all antigens, the appearances were identical to the fixed sections, except for poorer preservation of histological detail as expected. Frozen sections of a heart from a human CRP-treated rat killed at day 3 were also stained for human CRP by indirect immunofluorescence, and the nuclei counterstained with ethidium bromide, in order to visualize binding of CRP to cell surfaces.

Results

Figure 1:
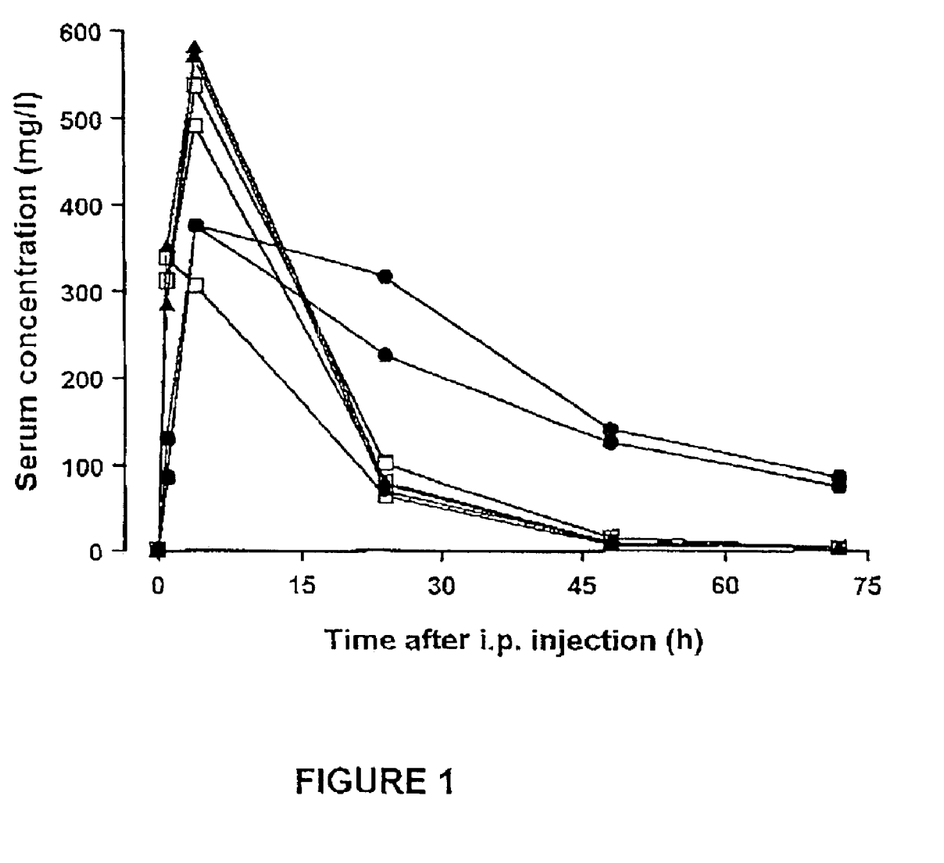
FIG. 1 shows a graph of serum concentration against time demonstrating plasma clearance of human CRP and SAP after injection into rats.

Infarct Size is Increased by Human CRP. We have previously shown that rat CRP does not activate rat complement whereas human CRP does so very efficiently[69]. The rat model therefore permits specific analysis of the complement-dependent effect of human CRP on infarct size in vivo. Rats which received 40 mg/kg of isolated pure human CRP by i.p injection 1 h after coronary artery ligation rapidly became clinically less well than buffer-treated controls, and some died during the next 3 d whilst receiving further daily injections of the same dose of human CRP. In contrast tats which had not been operated on but just received the same doses of human CRP showed absolutely no ill effects. Injections of human SAP, the pentraxin protein very closely related to CRP[1], had no adverse clinical effects in either normal or coronary artery ligated rats. When all surviving animals were killed on day 5 after coronary artery ligation, the infarcts in those receiving human CRP were about 40% larger than in control rats treated either with buffer or human SAP (Table 2). The plasma clearance of human CRP and SAP following single i.p. injections in control, non-operated rats, and the clearance of human CRP in decomplemented rats, are shown in FIG. 1. Each dataset represents values in a single animal. □, human CRP in untreated rats; ▲, human CRP in rats decomplemented by i.p. injection of 250 U/kg of cobra venom factor 24 h beforehand; ●, human SAP in untreated rats.

The clearance of human CRP was not affected by complement depletion. The peak values for human CRP were comparable to massive acute phase responses in man[2], and those for human SAP were much higher than ever seen in many[71]. Rats which have undergone coronary artery ligation do not survive the anesthesia required for bleeding and were therefore not bled before they were killed on day 5. However when these animals were killed 24 h after the last of 5 daily injections, the serum concentrations of human CRP were still in the range 13-53 mg/liter, typical of a moderate clinical acute phase response in man. In animals that had received human SAP, the serum concentrations of this protein were between 45 and 175 mg/liter. Values for rat CRP in serum at the time or exsanguination 5 d after coronary artery ligation were 215-525 mg/liter, which is within the normal range for this species[69].

Complement Dependence of the Enhancement of Infarct Size by Human CRP. Administration of cobra venom factor in vivo rapidly produces profound and sustained depletion of C3[70], with no active C3 remaining in the circulation at 6 h. Traces of C3 antigen detectable thereafter are inactive cleavage fragments[72]. With the dose of cobra venom factor used here, 250 U/kg[70], active C3 starts to reappear in the circulation after about 4 d and is within the normal range by day 5 or 6. When rats had been decomplemented by in vivo administration of cobra venom factor 24 h before coronary artery ligation, their infarcts at 5 d were about 60% smaller than in control untreated animals (Table 3). Complement sufficient rats injected daily with human CRP developed, as before, infarcts approximately 40% larger than those in control untreated animals. However, injection of human CRP had no effect at all on the reduced infarct size in decomplemented rats (Table 3). The damaging effect or human CRP in this model is thus absolutely complement dependent.

Figure 2:
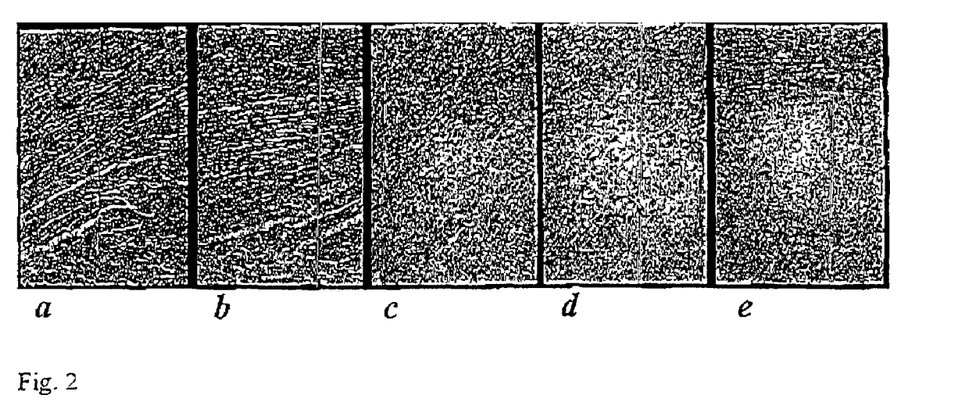
FIG. 2 shows the results of immunohistochemical staining of rat myocardial infarcts.

Deposition of CAR and Complement in Rat Myocardial Infarcts FIG. 2 shows the results of immunohistochemical staining of rat myocardial infarcts on day 5. a, hematoxylin and eosin stain showing infarcted myocardial cells and adjacent dense mononuclear cell infiltrate. b, immunostain with anti-human CRP with uptake localized to the infarcted area and both diffuse and focal patterns of immunoreactivity; many of the adjacent infiltrating macrophages are also immunoreactive. c, immunostain with anti-human CRP preabsorbed with isolated pure human CRP, showing complete absence of any staining and confirming the immunospecificity for human CRP of the pattern observed in b. d, immunostain with anti-rat C3 with uptake confined, in contrast to the anti-human CRP (b), to focal structures, possibly nuclear ghosts, within the infarct. e, Immunostain with anti-rat C3 preabsorbed with whole rat serum, showing complete absence of any staining. Absorption of the anti-rat C3 antibody with C3 depleted rat serum did not affect the staining pattern, confirming its immunospecificity for rat C3. Original magnifications, ×40. Human CRP and rat C3 (FIG. 2), and rat CRP (not shown), were all deposited in the infarcted myocardium. On day 5 human and rat CRP were present homogeneously throughout the infarcted muscle and also in a more intense, speckled pattern in multiple foci that occasionally coincided with hematoxyphil nuclear remnants. These foci may be nuclear ghosts from which chromatin has been cleared, but retaining the small nuclear ribonucleoprotein particles to which human CRP binds avidly[8,9] and possibly other CRP ligands. Rat C3 was present predominantly in the same speckled foci, with no diffuse immunoreactivity on the infarcted muscle cells, in contrast to the distribution of CRP. Immunofluorescence staining of sections of unfixed, snap frozen myocardial tissue taken 72 h after coronary ligation, clearly demonstrated the presence of CRP on the surface of damaged myocardial cells in and around the infarct, as well as the same distribution seen in fixed sections stained by the immunoperoxdase method. Staining for human CRP was always more intense than for rat CRP, although it is not clear whether this represents greater abundance of the human protein in the tissue sections, or just greater sensitivity of the respective immunostaining procedure. Numerous mononuclear cells in the dense peri-infarct infiltrate also stained strongly for human CRP (FIG. 2) but not for rat CRP (not shown) or rat C3 (FIG. 2).

Discussion

CRP has been very stably conserved in evolution[1,73,74] and no structural polymorphism or deficiency of CRP in man has yet been reported, suggesting that this protein has important normal functions that contribute to survival. In experimental models CRP is protective against pneumococcal infection[75,76] and may contribute to innate immunity to other micro-organisms to which it binds[13]. CRP also probably plays an important role in scavenging autologous ligands and preventing development of autoimmunity, by analogy with this role of SAP in relation to chromatin that we have recently demonstrated[77].

The present results unequivocally demonstrate, in a robust experimental model, that human CRP markedly enhances the extent of myocardial damage produced by ischemic injury. Although the time-concentration profile of human CRP produced by daily CRP injections was not the same as the monophasic acute phase response that follows uncomplicated naturally occurring myocardial infarction in man, it was comparable to the persistent, high and fluctuating CRP pattern typically found in patients with post-infarct complications[52], and was therefore not 'unphysiological'. Endogenous rat CRP, as well as the injected human CRP, was deposited in the infarct in vivo, but rat CRP does not activate rat complement[69]. In contrast human CRP is a potent activator of rat complement[69], and the enhancement of infarct size caused by administration of human CRP is completely abrogated by in vivo complement depletion Human CRP production is always greatly increased following acute myocardial infarction, CRP is always deposited in human myocardial infarcts, and early and late clinical outcomes are significantly associated with peak post-infarction plasma levels of CRP. It is therefore very likely that CRP contributes importantly to the extent of damage in human acute myocardial infarction and, based on our results here, it probably does so via complement activation. Although complement activation by CRP is not efficient in generating the terminal lytic complement complex, it very effectively cleaves C3, the critical step for opsonisation by C3b and liberation of the C3a anaphylatoxin.

These findings have important therapeutic implications, suggesting that a drug capable of inhibiting the binding of human CRP to its target ligands in vivo, and thereby preventing it from activating complement, should reduce infarct size with corresponding clinical benefit. Furthermore, increased CRP production is a feature of the non-specific acute phase response to a very wide range of traumatic, infectious, inflammatory and neoplastic tissue damaging conditions[2]. In all of these, including disorders as diverse as burns, surgical trauma, rheumatoid arthritis, sepsis and invasive neoplasia, there are non-irremediably damaged cells which, by analogy with myocardial infarction, are likely to be targeted by the opsonic and pro-inflammatory actions of CRP and complement. Specific inhibition of CRP binding in vivo might thus be expected to be of wide clinical benefit, and suitable compounds are currently being sought, supported by our recent description of the high resolution 3D structure of the physiological CRP-ligand complex[64].

TABLE 1

Percent Inhibition by Various Compounds of Binding of Radiolabelled CRP to Immobilized Enzyme Modified Low Density Lipoprotein

| | Molarity | | | | |
|---|---|---|---|---|---|
| Compound | 10 mM | 1 mM | 100 µM | 10 µM | 1 µM |
| None | 0 | 0 | 0 | 0 | 0 |
| Phosphoethanolamine | 92 | 90 | 39 | 0 | 0 |
| Phosphocholine | 95 | 94 | 93 | 46 | 0 |
| Hexadecyl phosphocholine | 94 | 73 | 76 | 0 | 0 |
| Phosphoserine | 38 | 0 | 0 | 0 | 0 |

TABLE 2

Human CRP Increases Myocardial Infarct Size in Rats

| Treatment | No. treated | Day 5 survivors | Infarct size mean (SD) % | Bonferroni t-test vs controls |
|---|---|---|---|---|
| Experiment 1 | | | | |
| Buffer only | 5 | 5 | 14.5 (1.1) | |
| Human CRP | 5 | 4 | 21.2 (2.0) | P = 0.0007 |
| Experiment 2 | | | | |
| Buffer only | 3 | 3 | 12.9 (0.9) | |
| Human SAP | 5 | 5 | 12.4 (1.9) | Not significant |
| Human CRP | 5 | 3 | 17.6 (0.4) | P = 0.0022 |

Human CRP or SAP were injected i.p. at 40 mg/kg

TABLE 3

Complement Dependence of the Enhancement of Infarct Size by Human CRP

| Treatment | No. treated | Day 5 survivors | Infarct size mean (SD) % | Bonferroni t-test vs controls |
|---|---|---|---|---|
| Buffer only | 8 | 8 | 14.3 (1.2) | |
| Human CRP | 5 | 3 | 19.7 (1.6) | P = 0.0020 |
| Complement depletion | 5 | 5 | 6.5 (0.9) | P = 0.0000 |
| Complement depletion + human CRP | 6 | 6 | 6.9 (0.3) | P = 0.0000 |

Human CRP at 40 mg/kg was injected i.p. 1 h after coronary artery ligation and then at 24 h intervals until all rats were killed on 5 d later; controls received just buffer alone. Parallel groups had been decomplemented by i.p. injection of cobra venom factor at 250 U/kg 24 h before coronary artery ligation.

REFERENCES

1. Pepys, M. B. and Baltz, M. L. (1983) Acute phase proteins with special reference to C-reactive protein and related proteins (pentaxins) and serum amyloid A protein. *Adv. Immunol.*, 34: 141-212.
2. Pepys, M. B. (1996) The acute phase response and C-reactive protein. *In: Oxford Textbook of Medicine, Third Ed.*, Vol. 2 (Weatherall, D. J., Ledingham, J. G. G. and Warrell, D. A., eds.), Oxford University Press, Oxford, pp. 1527-1533.

3. Volanakis, J. E. and Kaplan, M. F. (1971) Specificity of C-reactive protein for choline phosphate residues of pneumococcal C-polysaccharide. *Proc. Soc. Exp. Biol. Med.,* 136: 612-614.
4. de Beer, F. C., Soutar, A. K., Baltz, M. L., Trayner, I., Feinstein, A. and Pepys, M. B. (1982) Low density and very low density lipoproteins are selectively bound by aggregated C-reactive protein. *J. Exp. Med.,* 156: 230-242.
5. Pepys, M. B., Rowe, I. F. and Baltz, M. L. (1905) C-reactive protein: binding to lipids and lipoproteins *Int. Rev. Exp. Pathol.,* 27: 83-111.
6. Narkates, A. J. and Volanakis, J. E. (1982) C-reactive protein binding specificities: artificial and natural phospholipid bilayers. *Ann. N.Y. Acad. Sci.,* 389: 172-182.
7. Volanakis, J. E. and Wirtz, K. W. A. (1979) Interaction of C-reactive protein with artificial phosphatidylcholine bilayers. *Nature,* 281: 155-157.
8. Du Clos, T. W. (1999) C-reactive protein reacts with the U1 small nuclear ribonucleoprotein. *J. Immunol.,* 143: 2553-2559.
9. Pepys, M. B., Booth, S. E., Tennent, G. A., Butler, P. J. G. and Williams, D. G. (1994) Binding of pentraxins to different nuclear structures: C-reactive protein binds to small nuclear ribonucleoprotein particles, serum amyloid P component binds to chromatin and nucleoli. *Clin. Exp. Immunol.,* 97: 152-157.
10. Kindmark, C.-O. (1972) In vitro binding of human C-reactive protein by some pathogenic bacteria and zymosan. *Clin. Exp. Immunol.,* 11: 283-289.
11. Fletcher, T. C., White, A. and Baldo, B. A. (1980) Isolation of a phosphorylcholine-containing component from the turbot tapeworm, *Bothriocephalus scorpii* (Muller) and its reaction with C-reactive protein. *Parsite Immunol.,* 2: 237-248.
12. de Beaufort, A. J., Langermans, J. A. M., Matze-van der Lans, A. M., Hiemstra, P. S., Vossen, J. M. and Van Furth, R. (1997) Difference in binding of killed and live *Streptococcus pneumoniae* serotypes by C-reactive protein. *Scand. J. Immunol.,* 46: 597-600.
13. Weiser, J. N., Pan, N., McGowan, K. L., Musher, D., Martin, A. and Richards, J. (1998) Phosphorylcholine on the lipopolysaccharide of *Haemophilus influenzae* contributes to persistence in the respiratory tract and sensitivity to serum killing mediated by C-reactive protein. *J. Exp. Med.,* 187: 631-640.
14. Culley, F. J., Bodman-Smith, K. B., Ferguson, M. A. J., Nikolaev, A. V., Shantilal, N. and Raynes, J. G. (2000) C-reactive protein binds to phosphorylated carbohydrates. *Glycobiology,* 10: 59-65.
15. Lysenko, E., Richards, J. C., Cox, A. D., Stewart, A., Martin, A., Kapoor, M. and Weiser, J. N. (2000) The position of phosphorylcholine on the lipopolysaccharide or *Haemophilus influenzae* affects binding and sensitivity to C-reactive protein-mediated killing. *Mol. Microbiol.,* 35: 234-245.
16. Kaplan, M. H. and Volanakis, J. E. (1974) Interaction of C-reactive protein complexes with the complement system. I. Consumption of human complement associated with the reaction of C-reactive protein with pneumococcal C-polysaccharide and with the choline phosphatides, lecithin and sphingomyelin. *J. Immunol.,* 112: 2135-2147.
17. Volanakis, J. E. and Kaplan, M. H. (1974). Interaction of C-reactive protein complexes with the complement system. II. Consumption of guinea-pig complement by CRP complexes: requirement for human Clq. *J. Immunol.,* 113: 9-17.
18. Claus, D. R., Siegel, J., Petras, K., Osmand, A. P. and Gewurz, H. (1977) Interactions of C-reactive protein with the first component of human complement. *J. Immunol.,* 119: 187-192.
19. Volanakis, J. E. (1982) Complement activation by C-reactive protein complexes. *Ann. N.Y. Acad. Sci.,* 389: 235-250.
20. Mortensen, R. F., Osmand, A. P., Lint, T. E. and Gewurz, H. (1976) Interaction of C-reactive protein with lymphocytes and monocytes: complement-dependent adherence and phagocytosis. *J. Immunol.,* 117: 774-781.
21. Nakayama, S., Mold, C., Gewurz, H. and Du Clos, T. W. (1982) Opsonic properties at C-reactive protein in vivo. *J. Immunol.,* 128: 2435-2438.
22. Osmand, A. P., Mortensen, R. F., Siegel, J. and Gewurz, H. (1975) Interactions of C-reactive protein with the complement system. III. Complement-dependent passive hemolysis initiated by CRP. *J. Exp. Med.,* 142: 1065-1077.
23. Finland, M. and Dowling, H. F. (1935) Cutaneous reactions and antibody response to intracutaneous injections of pneumococcus polysaccharides. *J. Immunol.,* 29: 285-299.
24. Kushner, I. and Kaplan, M. H. (1961) Studies of acute phase protein. I. An immunohistochemical method for the localization of Cx-reactive protein in rabbits. Association with necrosis in local inflammatory lesions. *J. Exp. Med.,* 114: 961-973.
25. Kushner, I., Rakita, L. and Kaplan, M. H. (1963) Studies of acute phase protein. II. Localization of Cx-reactive protein in heart in induced myocardial infarction in rabbits. *J. Clin. Invest.,* 42: 286-292
26. Gitlin, J. D., Gitlin, J. I. and Gitlin, D. (1977) Localisation of C-reactive protein in synovium of patients with rheumatoid arthritis. *Arthritis Rheum.,* 20: 1491-1499.
27. Du Clos, T. W., Mold, C., Paterson, P. Y., Alroy, J. and Gewurz, H. (1981) Localization of C-reactive protein in inflammatory lesions of experimental allergic encephalomyelitis. *Clin. Exp. Immunol,* 43: 565-573
28. Lagrand, W. K., Niessen, H. W. M. , Wolbink, G.-J., Jaspars, L. H., Visser, C. A., Verheugt, F. W. A., Meijer, C. J. L. M. and Hack, C. E. (1997) C-reactive protein colocalizes with complement in human hearts during acute myocardial infarction. *Circulation,* 95: 97-103
29. Torzewski, J., Torzewski, M., Bowyer, D. E., Fröhlich, M., Koenig, W., Waltenberger, J., Fitzsimmons, C. and Hombach, V. (1998) C-reactive protein frequently colocalizes with the terminal complement complex in the intima of early atherosclerotic lesions of human coronary arteries. *Arterioscler. Thromb. Vasc. Biol.,* 18: 1336-1392.
30. Wolbink, G.-J., Bossink, A. W. J., Groeneveld, A. B. J., de Groot, M. C. M., Thijs, L. G. and Hack, C. E. (1998) Complement activation in patients with sepsis is in part mediated by C-reactive protein. *J. Infect. Dis.,* 177: 81-87.
31. Vigushin, D. M., Pepys, M. B. and Hawkins, P. N. (1993) Metabolic and scintigraphic studies of radioiodinated human C-reactive protein in health and disease. *J. Clin. Invest.,* 91: 1351-1357.
32. Kew, R. R., Hyers, T. M. and Webster, R. O. (1990) Human C-reactive protein inhibits neutrophil chemotaxis in vitro: possible implications for the adult respiratory distress syndrome. *J. Lab. Clin. Med.,* 115: 339-345.
33. Heuertz, R. M., Xia, D., Samols, D. and Webster, R. O. (1992) Transgenic mice expressing plasma rabbit C-reactive protein exhibit diminished vascular permeability and neutrophil infiltration in C5a-induced alveolitis. *FASEB J.,* 6: 1064 (abstract).

34. Mold, C. and Gewurz, H. (1980) Activation of the alternative pathway by liposomes: inhibitory effect of C-reactive protein. *Fed. Proc.,* 39: 702.

35. Mold, C. and Gewurz, H. (1981) Inhibitory effect of C-reactive protein on alternative C pathway activation by liposomes and *Streptococcus pneumoniae. J. Immunol.,* 127: 2089-2092.

36. Gershov, D., Kim, S., Brot, N. and Elkon, K. B. (2000) C-reactive protein binds to apoptotic cells, protects the cells from assembly of the terminal complement components, and sustains an antiinflammatory innate immune response: implications for systemic autoimmunity. *J. Exp. Med.,* 192: 1353-1363.

37. Shine, B., de Beer, P. C. and Pepys, M. B. (1931) Solid phase radioimmunoassays for C-reactive protein. *Clin. Chim. Acta,* 117: 13-23.

38. Hutchinson, W. L., Koenig, W., Fröhlich, M., Sund, M., Lowe, G. D. O. and Pepys, M. B. (2000) Immunoradiometric assay of circulating C-reactive protein: age-related values in the adult general population, *Clin. Chem.,* 46: 934-938.

39. Liuzzo, G., Biasucci, L. M., Gallimore, J. R., Grillo, R. L., Rebuzzi, A. G., Pepys, M. B. and Maseri, A. (1994) The prognostic value of C-reactive protein and serum amyloid A protein in severe unstable angina. *N. Engl. J. Med.,* 331: 417-424.

40. Kuller, L. H., Tracy, R. P., Shaten, J. and Meilahn, E. N. (1996) Relation of C-reactive protein and coronary heart-disease in the MRFIT nested case control study. *Am. J. Epidemiol.,* 144: 537-547.

41. Haverkate, F., Thompson, S. G., Pyke, S. D. M., Gallimore, J. R. and Pepys, M. B. (1997) Production of C-reactive protein and risk of coronary events in stable and unstable angina. *Lancet,* 349: 462-466.

42. Ridker, P. M., Cushman, M, Stampfer, M. J., Tracy, R. P. and Hennekens, C. H. (1997) Inflammation, aspirin, and the risk of cardiovascular disease in apparently healthy men. *N. Engl. J. Med.,* 336: 973-979.

43. Ridker, P. M., Cushman, M., Stampfer, M. J., Tracy, R. P. and Hennekens, C. H. (1998) Plasma concentration of C-reactive protein and risk of developing peripheral vascular disease. *Circulation,* 97: 425-428.

44. Ridker, P. M., Buring, J. E., Shih, J., Matias, M. and Hennekens, C. H. (1998) Prospective study of C-reactive protein and the risk of future cardiovascular events among apparently healthy women. *Circulation,* 98: 731-733.

45. Ridker, P. M. (1998) C-reactive protein and risks of future myocardial infarction and thombotic stroke. *Eur. Heart J.,* 19: 1-3.

46. Danesh, J., Collins, R., Appleby, P. and Peto, R. (1998) Association of fibrinogen, C-reactive protein, albumin, or leukocyte count with coronary heart disease. *J. Am. Coll. Cardiol.,* 279: 1477-1482.

47. Koenig, W., Sund, M., Fröhlich, M., Fischer, H.-G., Löwel, H., Döring, A., Hutchinson, W. L. and Pepys, M. B. (1999) C-reactive protein, a sensitive marker of inflammation, predicts future risk of coronary heart disease in initially healthy middle-aged men. Results from the MONICA (Monitoring Trends and Determinants in Cardiovascular Disease) Augsburg Cohort Study 1984 to 1992. *Circulation,* 99: 237-242.

48. Danesh, J., Whincup, P., Walker, M., Lennon, L., Thomson, A., Appleby, P., Gallimore, J. R. and Pepys, M. B. (2000) Low-grade inflammation and coronary heart disease: new prospective studies and updated meta-analyses. *B.M.J.,* 321: 199-204.

49. Zhang, Y. X., Cliff, W. J., Schoefl, G. I. and Higgins, G. (1999) Coronary C-reactive protein distribution: its relation to development of atherosclerosis. *Atherosclerosis,* 145: 375-379.

50. Bhakdi, S., Torzewski, M., Klouche, M. and Hemmes, M. (1999) Complement and atherogenesis. Binding of CRP to degraded, nonoxidized LDL enhances complement activation. *Arterioscler. Thromb. Vasc. Biol.,* 19: 2348-2354.

51. Cermak, J., Key, N. S., Bach, R. R., Balla, J., Jacob, H. S. and Vercellotti, G. M. (1993) C-reactive protein induces human peripheral blood monocytes to synthesize tissue factor. *Blood,* 82: 513-520.

52. de Beer, F. C., Hind, C. R. K., Fox, K. M., Allan, R, Maseri, A. and Pepys, M. B. (1982) Measurement of serum C-reactive protein concentration in myocardial ischaemia and infarction. *Br. Heart J.,* 47: 239-243.

53. Ueda, S., Ikeda, U., Yamamoto, K., Takahashi, M., Nishinaga, M., Nago, N. and Shimada, K. (1996) C-reactive protein as a predictor of cardiac rupture after acute myocardial infarction. *Am. Heart J,* 131: 857-860.

54. Pietilä, K. O., Harmoinen, A. P., Jokiniitty, J. and Pasternack, A. I. (1996) Serum C-reactive protein concentration in acute myocardial infarction and its relationship to mortality during 24 months of follow-up in patients under thrombolytic treatment. *Eur. Heart J.,* 17: 1345-1349.

55. Morrow, D. A., Rifai, N., Antman, E. M., Weiner, D. L., McCabe, C. H., Cannon, C. P. and Braunwald, E. (1998) C-reactive protein is a potent predictor of mortality independently of and in combination with troponin T in acute coronary syndromes: a TIMI 11A substudy. Thrombolysis in myocardial infarction. *J. Am. Coll. Cardiol.,* 31: 1460-1465.

56. Tommasi, S., Carluccio, E., Bentivoglio, M., Buccolieri, M., Mariotti, M.; Politano, M. and Corea, L. (1999) C-reactive protein as a marker for cardiac ischemic events in the year after a first, uncomplicated myocardial infarction. *Am. J. Cardiol.,* 83: 1595-1599.

57. de Winter, R. J., Bholasingh, R., Lijmer, J. G., Koster, R. W., Gorgels, J. P. M. C., Schouten, Y., Hoek, F. J. and Sanders, G. T. (1999) Independent prognostic value of C-reactive protein and troponin I in patients with unstable angina or non-Q-wave myocardial infarction. *Cardiovasc. Res.,* 42: 240-245.

58. Nikfardjam, M., Müllner, M., Schreiber, W., Oschatz, E., Exner, I., Domanovits, H., Laggner, A. N. and Huber, K. (2000) The association between C-reactive protein on admission and mortality in patients with acute myocardial infarction. *J. Intern. Med.,* 247: 341-345.

59. Beranek, J. T. (1997) C-reactive protein and complement in myocardial infarction and postinfarction heart failure. *Eur. Heart J.,* 18: 1834-1835.

60. Beranek, J. T. (1998) C-reactive protein in postinfarction heart rupture. *Am. Heart J.,* 136: 563-564.

61. van Leeuwen, M. A., van Rijswijk, M. H., Sluiter, W. J., van Riel, P. L. C. M., Kuper, I. H., van de Putte, L. B. A., Pepys, M. B. and Limburg, P. C. (1997) Individual relationship between progression of radiological damage and the acute phase response in early rheumatoid arthritis. Towards development of a decision support system. *J. Rheumatol.,* 24: 20-27.

62. Boralessa, H., de Beer, F. C., Manchie, A., Whitwam, J. G. and Pepys, M. B. (1986) C-reactive protein in patients undergoing cardiac surgery. *Anaesthesia,* 41: 11-15.

63. Shrive, A. K., Cheetham, G. M. T., Holden, D., Myles, D. A. A., Turnell, W. G., Volanakis, J. E., Pepys, M. B., Bloomer, A. C. and Greenhough, T. J. (1996) Three-dimensional structure of human C-reactive protein. *Nature Struct. Biology,* 3: 346-354

64. Thompson, D., Pepys, M. B. and Wood, S. P. (1999) The physiological structure of human C-reactive protein and its complex with phosphocholine. *Structure,* 7: 169-177.

65. Griselli, M., Herbert, J., Hutchinson, W. L., Taylor, K. M., Sohail, M., Krausz, T. and Pepys, M. B. (1999) C-reactive protein and complement are important mediators of tissue damage in acute myocardial infarction. *J. Exo. Med.,* 190: 1733-1740.

66. Bhakdi, S., Dorweiler, B., Kirchmann, R., Torzewski, J., Weise, E., Tranum-Jensen, J., Walev, I. and Wieland, E. (1995) On the pathogenesis of atherosclerosis: enzymatic transformation of human low density lipoprotein to an atherogenic moiety. *J. Exp. Med.,* 182: 1959-1971.

67. Hawkins, P. N., Tennent, G. A., Woo, P. and Pepys, M. S. (1991) Studies in vivo and in vitro of serum amyloid P component in normals and in a patient with AA amyloidosis. *Clin. Exp. Immunol.,* 84: 308-316.

68. Hawkins, P. N., Wootton, R. and Pepys, M. B. (1990) Metabolic studies of radioiodinated serum amyloid P component in normal subjects and patients with systemic amyloidosis. *J. Clin. Invest.,* 86: 1862-1869.

69. de Beer, F. C., Baltz, M. L., Munn, E. A., Feinstein, A., Taylor, J., Bruton, C., Clamp, J. R. and Pepys, M. B. (1982) Isolation and characterisation of C-reactive protein and serum amyloid P component in the rat. *Immunology,* 45: 55-70.

70. Pepys, M. B., Tompkins, C. and Smith, A. D. (1979) An improved method for the isolation from Naja naja venom of cobra factor (CoF) free of phospholipase A. *J. Immunol. Methods,* 30: 105-117.

71. Nelson, S. R., Tennent, G. A., Sethi, D., Gower, P. E., Ballardie, F. W., Amatayakul-Chantler, S. and Pepys, M. B. (1991) Serum amyloid P component in chronic renal failure and dialysis. *Clin. Chim. Acta,* 200: 191-200.

72. Pepys, M. B. (1975) Studies in vivo of cobra factor and murine C3. *Immunology,* 28: 369-377.

73. Pepys, M. B., Dash, A. C., Fletcher, T. C., Richardson, N., Munn, E. A. and Feinstein, A. (1979) Analogues in other mammals and in fish of human plasma proteins C-reactive protein and amyloid P component. *Nature,* 273: 168-170.

74. Baltz, M. L., de Beer, F. C., Feinstein, A., Munn, E. A., Milstein, C. P., Fletcher, T. C., March, J. F., Taylor, J., Bruton, C., Clamp, J. R., Davies, A. J. S. and Pepys, M. B. (1982) Phylogenetic aspects of C-reactive protein and related proteins. *Ann. N.Y. Acad. Sci.,* 389: 49-75.

75. Mold, C., Nakayama, S., Holzer, T. J., Gewurz, H. and Du Clos, T. W. (1981) C-reactive protein is protective against *Streptococcus pneumoniae* infection in mice. *J. Exp. Med.,* 154: 1703-1708.

76. Yother, J., Volanakis, J. E. and Briles, D. E. (1992) Human C-reactive protein is protective against fatal *Streptococcus pneumoniae* infection in mice. *J. Immunol.,* 128: 2374-2376.

77. Bickerstaff, M. C. M., Botto, M., Hutchinson, W. L., Herbert, J., Tennent, G. A., Bybee, A., Mitchell, D. A., Cook, H. T., Butler, P. J. G., Walport, M. J. and Pepys, M. B. (1999) Serum amyloid P component controls chromatin degradation and prevents antinuclear autoimmunity. *Nature Med.,* 5: 694-697.

The invention claimed is:

1. A method for reducing damage to heart muscle caused by C-reactive protein (CRP) in a patient who has suffered ischemic necrosis and is in need thereof, comprising inhibiting CRP binding to its ligands in vivo in the patient, by administering to the patient an effective amount of a compound that comprises phosphocholine or a derivative thereof, wherein the compound has the general formula (II)

wherein X is H or $C_1$ to $C_{20}$ hydrocarbyl, and Y is N substituted to form ammonium.

2. The method of claim 1 wherein the compound is bound by the calcium-dependent ligand binding site of CRP.

3. The method of claim 1, wherein X is $C_1$ to $C_{20}$ alkyl.

4. The method of claim 3, wherein X is $C_1$ to $C_{20}$ alkyl.

5. A method for reducing tissue damage caused by C-reactive protein (CRP) in a patient in need thereof who has suffered an inflammatory or tissue damaging condition comprising inhibiting CRP binding to its ligands in vivo within the patient, by administering to the patient an effective amount of a compound that comprises phosphocholine or a derivative thereof, wherein the compound has the general formula (II)

wherein X is H or $C_1$ to $C_{20}$ hydrocarbyl, and Y is N substituted to form ammonium.

6. The method of claim 5 wherein the compound is bound by the calcium-dependent ligand binding site of CRP.

7. The method of claim 5, wherein X is $C_1$ to $C_{20}$ alkyl.

8. The method of claim 7, wherein X is $C_{12}$ to $C_{20}$ alkyl.

9. The method of claim 5, wherein the inflammatory or tissue damaging condition is selected from one or more of ischemic necrosis or stroke.

* * * * *

UNITED STATES PATENT AND TRADEMARK OFFICE
CERTIFICATE OF CORRECTION

PATENT NO. : 7,390,795 B2
APPLICATION NO. : 09/737544
DATED : June 24, 2008
INVENTOR(S) : Mark B. Pepys Page 1 of 1

It is certified that error appears in the above-identified patent and that said Letters Patent is hereby corrected as shown below:

Column 22, Formula II, on both occurrences in claim 1 and claim 5, should appear as follows:

Column 22, line 29, in claim 4 "$C_1$" should be changed to -- $C_{12}$ --.

Signed and Sealed this

Twenty-first Day of October, 2008

JON W. DUDAS
*Director of the United States Patent and Trademark Office*